(12) United States Patent
Mao et al.

(10) Patent No.: US 7,049,404 B2
(45) Date of Patent: May 23, 2006

(54) POLYPEPTIDE HUMAN POLYADENYLATION BINDING PROTEIN 20.13 AND POLYNUCLEOTIDE ENCODING IT

(75) Inventors: Yumin Mao, Shanghai (CN); Yi Xie, Shanghai (CN)

(73) Assignee: Shanghai Bio Window Gene Development Inc., Shanghai (CN)

( * ) Notice: Subject to any disclaimer, the term of this patent is extended or adjusted under 35 U.S.C. 154(b) by 8 days.

(21) Appl. No.: 10/362,238

(22) PCT Filed: Aug. 20, 2001

(86) PCT No.: PCT/CN01/01259

§ 371 (c)(1),
(2), (4) Date: Feb. 21, 2003

(87) PCT Pub. No.: WO02/26972

PCT Pub. Date: Apr. 4, 2002

(65) Prior Publication Data

US 2004/0053827 A1    Mar. 18, 2004

(30) Foreign Application Priority Data

Aug. 23, 2000  (CN)  .............................. 00 1 19744

(51) Int. Cl.
*C07K 1/00*     (2006.01)
*C07H 21/04*    (2006.01)

(52) U.S. Cl. ...................................... 530/350; 536/23.5
(58) Field of Classification Search ............... 536/23.1, 536/23.5; 435/4, 7.1
See application file for complete search history.

(56) References Cited

U.S. PATENT DOCUMENTS 5,824,875 A    10/1998  Ranu

OTHER PUBLICATIONS

Grange et al. Human mRNA polyadenylate binding protein: evolutionary conservation of a nucleic acid binding motif. Nucleic acids research, vol. 15, pp. 4771-4787, 1987.*
Deo et al. Recognition of polyadenylate RNA by the Poly(A)-binding protein. Cell, vol. 98, pp. 835-845, 1999.*
International Search Report.

* cited by examiner

*Primary Examiner*—Celian Qian
*Assistant Examiner*—Quang Nguyen
(74) *Attorney, Agent, or Firm*—Crowell & Moring LLP

(57) ABSTRACT

Novel human polyadenylation binding Protein 20.13 and polynucleotide encoding it. The invention also concerns the process of producing the polypeptide by recombinant DNA technique, and methods for treating many diseases e.g. disorder of embryo development, growth developmental disturbant diseases etc. The invention also discloses antagonists against the polypeptide.

2 Claims, 1 Drawing Sheet

Identity = 104/120 (86%), Similarity = 113/120 (94%)

```
Query:   1   MNASGSGYPLASLYVGDLHPDVTEAMLYEKFSPAGPILSIRVCRDVATRRSLGYAYINFQ  60
             MN S   YP+ASLYVGDLHPDVTEAMLYEKFSPAGPILSIRVCRD+ TRRSLGYAY+NFQ
Sbjct:   1   MNPSAPSYPMASLYVGDLHPDVTEAMLYEKFSPAGPILSIRVCRDMITRRSLGYAYVNFQ  60

Query:   61  QPADAERALDTMNFEMLKGQPIRIMWSQRDPGLRKSGVGNIFIKNLEDSIDNKALYDTFS  120
             QPADAERALDTMNF+++KG+P+RIMWSQRDP LRKSGVGNIFIKNL+ SIDNKALYDTFS
Sbjct:   61  QPADAERALDTMNFDVIKGKPVRIMWSQRDPSLRKSGVGNIFIKNLDKSIDNKALYDTFS  120

Query:       human polyadenylation binding Protein 20.13

Sbjct:       human polyadenylation binding Protein
```

Fig. 1

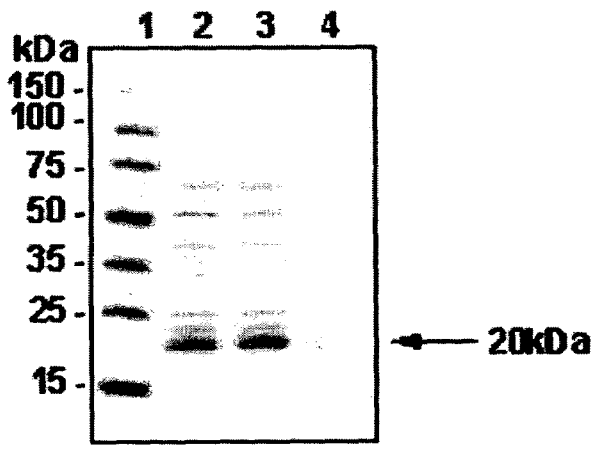

Fig. 2

SEQUENCE LISTING

<160> NUMBER OF SEQ ID NOS: 9

<210> SEQ ID NO 1
<211> LENGTH: 1916
<212> TYPE: DNA
<213> ORGANISM: Homo sapiens
<220> FEATURE:
<221> NAME/KEY: CDS
<222> LOCATION: (23)..(574)
<223> OTHER INFORMATION:

<400> SEQUENCE: 1

```
gagccccggc cccctgccca cc atg aac gcc agc ggt tct ggc tac ccg ctt         52
                         Met Asn Ala Ser Gly Ser Gly Tyr Pro Leu
                           1               5                  10 gcc tcg ctt tac gtg ggc gat ctg cac ccc gac gtg acc gag gcc atg         100
Ala Ser Leu Tyr Val Gly Asp Leu His Pro Asp Val Thr Glu Ala Met
                 15                  20                  25 ctc tat gag aag ttc tct ccc gcc ggc ccc atc ctg tcc atc cgc gtg         148
Leu Tyr Glu Lys Phe Ser Pro Ala Gly Pro Ile Leu Ser Ile Arg Val
             30                  35                  40 tgc cgc gat gta gcc acc cgg cgc tcg ctg ggc tac gcc tac atc aac         196
Cys Arg Asp Val Ala Thr Arg Arg Ser Leu Gly Tyr Ala Tyr Ile Asn
         45                  50                  55 ttc cag cag ccc gcg gac gcg gag cgg gca ctg gac aca atg aac ttt         244
Phe Gln Gln Pro Ala Asp Ala Glu Arg Ala Leu Asp Thr Met Asn Phe
     60                  65                  70 gag atg ctc aaa ggc cag cct att cgc atc atg tgg tcc cag cga gac         292
Glu Met Leu Lys Gly Gln Pro Ile Arg Ile Met Trp Ser Gln Arg Asp
 75                  80                  85                  90 cca gga ctt cgc aag tca ggt gtg ggc aac atc ttc atc aag aac ctg         340
Pro Gly Leu Arg Lys Ser Gly Val Gly Asn Ile Phe Ile Lys Asn Leu
                 95                 100                 105 gag gac tcc att gac aac aag gct tta tat gat acc ttc tcc acc agt         388
Glu Asp Ser Ile Asp Asn Lys Ala Leu Tyr Asp Thr Phe Ser Thr Ser
             110                 115                 120 tgt gcc tcg gcg ccc ccc ggc cca cat cag cag tgt cag gca ggc ctc         436
Cys Ala Ser Ala Pro Pro Gly Pro His Gln Gln Cys Gln Ala Gly Leu
         125                 130                 135 cac cca ggt gcc acg cac ggt gcc tca tac cca gag agt agc caa cat         484
His Pro Gly Ala Thr His Gly Ala Ser Tyr Pro Glu Ser Ser Gln His
     140                 145                 150 tgg tac tca gac cac agg acc cag tgg ggt agg atg ctg tac acc agg         532
Trp Tyr Ser Asp His Arg Thr Gln Trp Gly Arg Met Leu Tyr Thr Arg
155                 160                 165                 170 ccg gcc gct cct gcc gtg caa atg ttc ctc agc agc aca tag              574
Pro Ala Ala Pro Ala Val Gln Met Phe Leu Ser Ser Thr
                 175                 180 cacctatcgg gtccaggagc cggctgtgca catcccagga caggagcccc tgaccgcgtc     634
catgctggct gcggcgcccc tgcatgagca aaagcagatg attggcccag agacggaaag     694
```

-continued

```
tacaaagact agtaaaatac atccttgccc ttaaggagct aagtacccaa aacctgtaat    754
ccatcttgag tcaccagagt acggttgctc agaaacagca gtggtgcggt ggaaagggca    814
tcaaccctgc gatccggaca agtcactcca tccctctgat catgcgtgcc cacttaccac    874
atgaggatat cacttcatag acttgctgga agggttcatt gtgttagcct gttccctgag    934
ctctcttcgt gatcaagaag actgatcaga taaatcaaga gacttgccca aaattaccta    994
ggaaatctgt agcagcagca gaaccaaact ccggtccttg ctaaatctag ataccaggct   1054
agctcttcta tggacccaga attaacccat acaaatgtac aagcttttcc agaccagctg   1114
gggtgagatg aatgaaaatg gcagcaacat caatacctca gcttcttcag caacttcatc   1174
aagtaaggct gccatgagga agtgggccta aggagagtt ttctagaaca agaaggggg    1234
caaaggagtg gcttgaaact gcaaaaagtg cagacaaaaa aaaaaaaaag aatgaaatct   1294
ggagaggatg tgaggagagg tctagcaaaa tgattaaaaa tttggactta gcatcaaagt   1354
caaacagatc catattcaaa tcgtggctct tccatgtctt cactatgtaa ccccgaggga   1414
gccaatttaa ctctcttgga ctcctccttt ctaagcattt tatccacagg gccataataa   1474
agatcaaagg agatcgtgtc taaaatgtct agcacatggt aaatcactca agagatgcta   1534
gccaagaaaa ggaaaaaaag gaaggcggca aagggaaata ggtactgaac ggtgactcac   1594
agaaaccagg atccaaggct cctttcaaaa gtcaaggctt taaccaatga gggtttctga   1654
ttaagtcacc ctggagaagg ggctttgggc aaaggtctgc ggtatgctga cgaaagctgg   1714
acgctgggag aactggtaag aatatgctat ttttctgttt caaactctcc agtagcttcc   1774
catccagcaa ctttcatgcc aagcttccag tttggcatga aatccgaact ccttagcaga   1834
gtttacaaca cctccacaat aaataagggt ctgccttcct aaccgaaaaa aaaaaaaaac   1894
atgtcggccg cctcggccta tg                                           1916
```

<210> SEQ ID NO 2
<211> LENGTH: 183
<212> TYPE: PRT
<213> ORGANISM: Homo sapiens

<400> SEQUENCE: 2

```
Met Asn Ala Ser Gly Ser Gly Tyr Pro Leu Ala Ser Leu Tyr Val Gly
 1               5                  10                  15

Asp Leu His Pro Asp Val Thr Glu Ala Met Leu Tyr Glu Lys Phe Ser
                20                  25                  30

Pro Ala Gly Pro Ile Leu Ser Ile Arg Val Cys Arg Asp Val Ala Thr
            35                  40                  45

Arg Arg Ser Leu Gly Tyr Ala Tyr Ile Asn Phe Gln Gln Pro Ala Asp
        50                  55                  60

Ala Glu Arg Ala Leu Asp Thr Met Asn Phe Glu Met Leu Lys Gly Gln
65                  70                  75                  80

Pro Ile Arg Ile Met Trp Ser Gln Arg Asp Pro Gly Leu Arg Lys Ser
                85                  90                  95

Gly Val Gly Asn Ile Phe Ile Lys Asn Leu Glu Asp Ser Ile Asp Asn
            100                 105                 110

Lys Ala Leu Tyr Asp Thr Phe Ser Thr Ser Cys Ala Ser Ala Pro Pro
        115                 120                 125

Gly Pro His Gln Gln Cys Gln Ala Gly Leu His Pro Gly Ala Thr His
    130                 135                 140

Gly Ala Ser Tyr Pro Glu Ser Ser Gln His Trp Tyr Ser Asp His Arg
```

```
                    145                 150                 155                 160
Thr Gln Trp Gly Arg Met Leu Tyr Thr Arg Pro Ala Ala Pro Ala Val
                165                 170                 175

Gln Met Phe Leu Ser Ser Thr
            180

<210> SEQ ID NO 3
<211> LENGTH: 24
<212> TYPE: DNA
<213> ORGANISM: Artificial
<220> FEATURE:
<223> OTHER INFORMATION: oligonucleotide primer

<400> SEQUENCE: 3
gagccccggc ccctgccca ccat                                         24

<210> SEQ ID NO 4
<211> LENGTH: 24
<212> TYPE: DNA
<213> ORGANISM: Artificial
<220> FEATURE:
<223> OTHER INFORMATION: oligonucleotide primer

<400> SEQUENCE: 4
cataggccga ggcggccgac atgt                                        24

<210> SEQ ID NO 5
<211> LENGTH: 33
<212> TYPE: DNA
<213> ORGANISM: Artificial
<220> FEATURE:
<223> OTHER INFORMATION: oligonucleotide primer

<400> SEQUENCE: 5
ccccatatga tgaacgccag cggttctggc tac                              33

<210> SEQ ID NO 6
<211> LENGTH: 33
<212> TYPE: DNA
<213> ORGANISM: Artificial
<220> FEATURE:
<223> OTHER INFORMATION: oligonucleotide primer

<400> SEQUENCE: 6
cccgaattcc tatgtgctgc tgaggaacat ttg                              33

<210> SEQ ID NO 7
<211> LENGTH: 15
<212> TYPE: PRT
<213> ORGANISM: Artificial
<220> FEATURE:
<223> OTHER INFORMATION: partial sequence of SEQ ID NO: 2

<400> SEQUENCE: 7

Met Asn Ala Ser Gly Ser Gly Tyr Pro Leu Ala Ser Leu Tyr Val
  1               5                   10                  15

<210> SEQ ID NO 8
<211> LENGTH: 41
<212> TYPE: DNA
<213> ORGANISM: Artificial
<220> FEATURE:
<223> OTHER INFORMATION: oligonucleotide primer

<400> SEQUENCE: 8
```

```
tgaacgccag cggttctggc tacccgcttg cctcgcttta c                    41

<210> SEQ ID NO 9
<211> LENGTH: 41
<212> TYPE: DNA
<213> ORGANISM: Artificial
<220> FEATURE:
<223> OTHER INFORMATION: oligonucleotide primer

<400> SEQUENCE: 9
tgaacgccag cggttctggc cacccgcttg cctcgcttta c                    41
```

POLYPEPTIDE HUMAN POLYADENYLATION BINDING PROTEIN 20.13 AND POLYNUCLEOTIDE ENCODING IT

FIELD OF THE INVENTION

The invention relates to the field of biotechnology. In particular, the invention relates to a novel polypeptide, human polyadenylation binding Protein 20.13, and a polynucleotide sequence encoding said polypeptide. The invention also relates to the method for the preparation and use of said polynucleotide and polypeptide.

TECHNICAL BACKGROUND

Human poly (A) binding protein (PABP) is an evolutionarily conservative nucleotide binding domain and an important eukaryotic RNA binding protein. It is highly conservative and regulates translation initiation, mRNA stability and also the length of poly (A) tail in polyadenylation reaction, and must be blocked by messenger ribonucleoprotein (mRNP) during early embryogenesis. PABP functions as an important regulator in gene expression by controlling translation initiation.

Grange T. et al. cloned the cDNA of Human poly (A) binding protein (PABP) in 1999. It is a new member of terminal oligo pyramine protein family. Members of the family have an oligo pyridine in their 5'-terminus and encode complexes involved in translation, especially in translation control of developmental regulation. PABP gene has 15 exons whose total length is 2.86 kb, and 14 introns of the length 22 kb. 5'-UTR of human PBRP consists of 505 nucleotides which is far longer than the average length (44+/−4) of those of other vertebrates, which indicates it may have other regulation functions. There is an A rich region in human PABP gene from 73 to 123 bp, which participates in repression of PABP translation, and PABP may self-regulate its expression by binding the 5'-UTR. Developmental-dependent translation regulation of PABP mRNA is often associated to oligo pyridine in its 5' terminus. Replacement of the cytosine in its capped site by a purine leads to loss of its translation regulation function. That cytosine and nearly 30 nucleotides around it form a complex which encodes many translation related proteins such as ribosomal proteins, elongation factors 1α and 2 (EF1α and EF2), and involved in cis-mediated regulation of developmental-dependent translation by translation factors. Transcription of PABP gene usually begins from one or two cytosine in oligo pyridine chain and its mRNA is 29 kb. Its translation product is a 70,244 dalton protein. Human PABP is highly homologous to yeast PABP at the N-terminus and has relatively high level of poly (A) binding activity (Nucl. Aci. Res, 1987, 15 (12): 4771–4787). Number of the repeating subunits composed of nearly 80 amino acids is four times that of other nucleotide binding proteins. Its C-terminus is also similar to that of its yeast homolog, having 150 amino acid sequence and rich in proline, alanine, and glutamic acid, which amount for a very high percentage of about 48% of all amino acid sequence (J. Biol. C., 1999, 274 (3), 1708–1714).

Novel polypeptide of the present invention shares 86% homology and 94% similarity at the protein level with the known human poly (A) binding protein, and they also have similar structural characteristics, molecular weight, isoelectric point and peptide map. Thus this polypeptide is thought to be a component of an novel human poly (A) binding protein and named "human poly (A) binding protein 20.13," which has similar biological functions of the known protein, including protein translation regulation and RNA stability. Overexpression of this polypeptide will cause developmental abnormality. Besides, it can be used in diagnosis and treatment of related diseases.

As above-described human polyadenylation binding Protein 20.13 plays an essential role in the regulation of important biological functions such as cell division and embryogenesis, and it is believed that lots of proteins are involved in these regulations. So the determination of those related human polyadenylation binding Protein 20.13 of actin-binding proteins, especially of their amino acid sequences is always desired in this field. The isolation of this novel human polyadenylation binding Protein 20.13 builds the basis for research of the protein function under normal and clinical conditions and this protein can be the basis of disease diagnosis and/or drug development. So the isolation of its cDNA is very important.

DISCLOSURE OF THE INVENTION

One objective of the invention is to provide an isolated novel polypeptide, i.e., a human polyadenylation binding Protein 20.13, and its fragments, analogues and derivatives thereof.

Another objective of the invention is to provide a polynucleotide encoding said polypeptide.

Another objective of the invention is to provide a recombinant vector containing a polynucleotide encoding a human polyadenylation binding Protein 20.13.

Another objective of the invention is to provide a genetically engineered host cell containing a polynucleotide encoding a human polyadenylation binding Protein 20.13.

Another objective of the invention is to provide a method for producing a human polyadenylation binding Protein 20.13.

Another objective of the invention is to provide an antibody against a human polyadenylation binding Protein 20.13 of the invention.

Another objective of the invention is to provide mimetics, antagonists, agonists, and inhibitors for the polypeptide of the human polyadenylation binding Protein 20.13.

Another objective of the invention is to provide a method for the diagnosis and treatment of the diseases associated with an abnormality of human polyadenylation binding Protein 20.13.

SUMMARY OF THE INVENTION

The present invention relates to an isolated polypeptide, which is originated from human, and comprises a polypeptide having the amino acid sequence of SEQ ID NO: 2, or its conservative mutants, or its active fragments, or its active derivatives and its analogues. Preferably, the polypeptide has the amino acid sequence of SEQ ID NO: 2.

The present invention is also involved with an isolated polynucleotide, comprising a nucleotide sequence or its variant selected from the group consisting of:

(a) a polynucleotide encoding a polypeptide comprising the amino acid sequence of SEQ ID NO.2;

(b) a polynucleotide complementary to the polynucleotide (a); and (c) a polynucleotide shares at least 86% homology to the polynucleotide (a) or (b).

More preferably, said nucleotide sequence is selected from the group consisting of (a) the sequence of position 23–574 in SEQ ID NO: 1; and (b) the sequence of position 1–1916 in SEQ ID NO: 1.

The invention also includes: a vector containing the polynucleotides of said invention, especially an expression vector; a host cell genetically engineered with the vector and the host cell via transformation, transduction and transfection; a method for the production of the polypeptide through the process of host cell cultivation and expression product harvest.

The said invention also involves an antibody which specifically binds to the polypeptide.

The invention also includes a method for selection of compounds which simulate, activate, antagonize, or repress the activity of human polyadenylation binding Protein 20.13, and compounds obtained by the said method.

The invention also includes a method for in vitro assay of the diseases or disease susceptibility related to abnormal expression of human polyadenylation binding Protein 20.13. The method involves mutation detection of the said polypeptide or its encoding polynucleotide sequence, or the quantitative determination or biological activity assay of the polypeptide in biological samples.

The invention also includes a pharmaceutical composition which comprises the inventive polypeptide, its mimetic, its agonist, its antagonist, or its repressor, and a pharmaceutically acceptable carrier.

The invention also includes application of the inventive polypeptide and/or its polynucleotide for drug development to treat cancers, developmental diseases, immune diseases, or other diseases caused by abnormal expression of human polyadenylation binding Protein 20.13.

Other aspects of the invention are apparent to the skilled in the art in view of the disclosure.

BRIEF DESCRIPTION OF THE DRAWINGS

The following drawings are provided to illustrate the embodiment of the invention, not to limit the scope of invention defined by the claims.

FIG. 1 shows an alignment comparison of amino acid sequences of human polyadenylation binding Protein 20.13 (SEQ ID NO: 10) of the invention and human polyadenylation binding Protein. The upper sequence is human polyadenylation binding Protein 20.13, (SEQ ID NO: 11) and the lower sequence is human polyadenylation binding Protein. The identical and similar amino acids are indicated by a one-letter code of amino acid and "+" respectively.

FIG. 2 shows the SDS-PAGE of the isolated human polyadenylation binding Protein 20.13 which has a molecular weight of 20.13 kDa. The isolated protein band is marked with an arrow.

DESCRIPTION OF THE INVENTION

The terms used in this specification and claims have the following meanings, unless otherwise specifically noted.

"Nucleotide sequence" refers to oligonucleotide, nucleotide, or polynucleotide and parts of a polynucleotide. It also refers to genomic or synthetic DNA or RNA, which could be single stranded or double stranded, and could represent the sense strand or the antisense strand. Similarly, the term "amino acid sequence" refers to oligopeptide, peptide, polypeptide, or protein sequence and parts of proteins. When the "amino acid sequence" in said invention is related to the sequence of a natural protein, the amino acid sequence of said "peptide" or "protein" will not be limited to be identical to the sequence of that natural protein.

"Variety" or "variant" of a protein or polynucleotide refers to the amino acid sequence with one or several amino acid changed, or its encoding polynucleotide sequence with one or several nucleotides changed. Such changes include deletion, insertion, or substitution of one ore more amino acids in the amino acid sequence, or of nucleotides in the polynucleotide sequence. These changes could be conservative and the substituted amino acid has similar structure or chemical characteristics as the original one, just as the substitution of lie with Leu. Changes also could be not conservative, just as the substitution of Ala with Trp.

"Deletion" refers to the deletion of one or mroe amino acids in the amino acid sequence, or of one or more nucleotides in the nucleotide sequence.

"Insertion" or "addition" refers to the addition of one or several amino acids in the amino acid sequence, or of one or several nucleotides in the nucleotide sequence, comparing to the natural molecule. "Substitution" refers to the change of one or several amino acids, or of one or several nucleotides, into different ones without changing their number.

"Biological activity" refers to a protein with a natural structural, regulatory or biochemical functions. Similarly, the term "immunologic competence" refers to the ability of natural, recombinant, or synthetic proteins to induce a specific immune reaction, or to bind specific antibody in an appropriate animal or cell.

"Agonist" refers to the molecule which could regulate the activity of human polyadenylation binding Protein 20.13 by binding to or otherwise changing it. Agonists include proteins, nucleotides, carbohydrates or any other molecules which could bind to the human polyadenylation binding Protein 20.13.

"Antagonist" or "repressor" refers to the molecules which could repress or downregulate the biological activity or immune activity of human polyadenylation binding Protein 20.13 when bound to it. Antagonists or repressors include proteins, nucleotides, carbohydrates or any other molecules which could bind the human polyadenylation binding Protein 20.13.

"Regulation" refers to a functional change of human polyadenylation binding Protein 20.13, including increase or decrease of the protein activity, changes in binding specificity, changes of any other biological, functional or immune characteristics of human polyadenylation binding Protein 20.13.

"Substantially pure" refers to the condition of purity without any other natural related proteins, lipids, saccharides, or other substances. Ordinarily skilled artisans in this field can purify human polyadenylation binding Protein 20.13 by standard protein purification techniques. Substantially pure human polyadenylation binding Protein 20.13 produces a single main band in denaturing polyacrylamide gel. The purity of human polyadenylation binding Protein 20.13 can be analyzed by amino acid sequence analysis.

"Complementary" or "complementation" refers to the natural conjugation of polynucleotides by base pairing under the condition of suitable ion concentration and temperature. For instance, the sequence "C-T-G-A" could bind to its complementary sequence "G-A-C-T." The complementation between two single strand molecules could be partial or complete. Complementary degree between two single strands has obvious influence on hybrid efficiency and intensity of the nucleotides.

"Homology" refers to the complementary degree, which may be partially or completely homologous. "Partial homology" refers to a kind of partially complementary sequence when compared to a target nucleotide, and the sequence could at least partially repress the hybridization between a completely complementary sequence and the target nucleotide. Repression of the hybridization could be assayed by hybridization (Southern blot or Northern blot) under a lower stringency condition. Substantially complementary sequence or hybrid probe could compete with the completely complementary sequence and repress its hybridization with the target sequence under a lower stringency condition. This effect does not mean that nonspecific binding is allowed under a lower stringency condition, because specific or selective reaction is still required for hybridization under a lower stringency condition.

"Identity percentage" or "percent identity" refers to the percentage of sequence identity or similarity when two or several amino acid or nucleotide sequences are compared. Identity percentage could be determined by computational methods such as the MEGALIGN program (Lasergene software package, DNASTAR, Inc., Madison Wis.). MEGALIGN program can compare two or several sequences with different kinds of methods such as Cluster method (Higgins, D. G. And P. M. Sharp (1988) Gene 73:237–244). Cluster method examines the distance between all pairs and arranges the sequences into clusters. Then the clusters are partitioned by pair or group. The identity percentage between two amino acid sequences, A and B, can be calculated by the following equation:

$$\frac{\text{Number of paired residues between sequences } A \text{ and } B}{\text{Residue number of sequence } A - } \times 100$$
$$\text{number of spacing residues in sequence } A -$$
$$\text{number of spacing residue in sequence } B$$

Identity percentage between nucleotide sequences can also be determined by the Cluster method or other well-known methods in this field such as the Jotun Hein method (Hein J., Methods in Emzymology, 1990, 183:625–645).

"Similarity" refers to the identical degree or conservative substitution degree of amino acid residues in corresponding sites of the amino acid sequences when compared to each other. Amino acids for conservative substitution are e.g. among negative charged amino acids (e.g., Asp and Glu); among positive charged amino acids (including Leu, Ile and Val); between Gly and Ala; between Asn and Gln; between Ser and Thr; and between Phe and Tyr.

"Antisense" refers to the nucleotide sequences complementary to a specific DNA or RNA sequence. "antisense strand" refers to the nucleotide strand complementary to the "sense strand."

"Derivative" refers to HFP or the chemically modified nucleotide encoding it. This kind of modified chemical can be derived from replacement of the hydrogen atom with an alkyl, acyl, or amino group. The nucleotide derivative can encode peptide remaining the major biological characteristics of the natural molecule.

"Antibody" refers to an intact antibody or its fragments such as Fa, F (ab')$_2$ and Fv, and it can specifically bind antigenic determinants of human polyadenylation binding Protein 20.13.

"Humanized antibody" refers to an antibody which has its amino acid sequence in non-antigen binding region replaced to mimic human antibody and still retain the original binding activity.

The term "isolated" refers to the removal of a material out of its original environment (for instance, if it is naturally produced, original environment refers to its natural environment). For example, a naturally produced polynucleotide or a peptide in a living organism means it has not been "isolated." While the separation of the polynucleotide or a peptide from its coexisting materials in natural system means it is "isolated." This polynucleotide may be a part of a vector. This polynucleotide or peptide may also be part of a compound. Since the vector or compound is not part of its natural environment, the polynucleotide or peptide is still "isolated."

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated human polyadenylation binding Protein 20.13," means that human polyadenylation binding Protein 20.13, does not essentially contain other proteins, lipids, carbohydrates or any other substances associated therewith in nature. Those skilled in the art can purify human polyadenylation binding Protein 20.13, by standard protein purification techniques. The purified polypeptide forms a single main band on a non-reductive PAGE gel. The purity of human polyadenylation binding Protein 20.13 can be analyzed by amino acid sequence analysis.

The invention provides a novel polypeptide—human polyadenylation binding Protein 20.13, which comprises the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacterial, yeast, higher plant, insect, and mammal cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of human polyadenylation binding Protein 20.13. As used in the invention, the terms "fragment", "derivative" and "analogue" mean the polypeptide that essentially retains the same biological functions or activity of human polyadenylation binding Protein 20.13 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, include a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 1916 bp, whose ORF (23–574) encodes 183 amino acids. Based on amino acid homology comparison, it is found that the encoded polypeptide is 86% homologous to human polyadenylation binding Protein. This novel human polyadenylation binding Protein 20.13 has similar structures and biological functions to those of the human polyadenylation binding Protein.

The polynucleotide according to the invention may be in the forms of DNA or RNA. The forms of DNA include cDNA, genomic DNA, and synthetic DNA, etc., in single stranded or double stranded form. DNA may be an encoding strand or non-encoding strand. The coding sequence for mature polypeptide may be identical to the coding sequence shown in SEQ ID NO: 1, or is a degenerate sequence. As used herein, the term "degenerate sequence" means an sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 includes those encoding only the mature polypeptide, those encoding mature polypeptide plus various additional coding sequence, the coding sequence for mature polypeptide (and optional additional encoding sequence) plus the non-coding sequence.

The term "polynucleotide encoding the polypeptide" includes polynucleotides encoding said polypeptide and polynucleotides comprising additional coding and/or non-coding sequences.

The invention further relates to variants of the above polynucleotides which encode a polypeptide having the same amino acid sequence of invention, or a fragment, analogue and derivative of said polypeptide. The variant of the polynucleotide may be a naturally occurring allelic variant or a non-naturally occurring variant. Such nucleotide variants include substitution, deletion, and insertion variants. As known in the art, an allelic variant may have a substitution, deletion, and insertion of one or more nucleotides without substantially changing the functions of the encoded polypeptide.

The present invention further relates to polynucleotides, which hybridize to the herein above-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and high temperature, such as 0.2×SSC, 0.1% SDS, 60° C.; or (2) hybridization after adding denaturants, such as 50% (v/v) formamide, 0.1% bovine serum/ 0.1% FicoII, 42° C.; or (3) hybridization only when the homology of two sequences at least 95%, preferably 97%. Further, the polynucleotides which hybridize to the hereinabove described polynucleotides encode a polypeptide which retains the same biological function and activity as the mature polypeptide of SEQ ID NO: 2

The invention also relates to nucleic acid fragments hybridized with the herein above sequence. As used in the present invention, the length of the "nucleic acid fragment" is at least more than 10 bp, preferably at least 20–30 bp, more preferably at least 50–60 bp, and most preferably at least 100 bp. The nucleic acid fragment can be used in amplification techniques of nucleic acid, such as PCR, so as to determine and/or isolate the polynucleotide encoding human polyadenylation binding Protein 20.13.

The polypeptide and polynucleotide of the invention are preferably in the isolated form, preferably purified to be homogenous.

According to the invention, the specific nucleic acid sequence encoding human polyadenylation binding Protein 20.13 can be obtained in various ways. For example, the polynucleotide is isolated by hybridization techniques well-known in the art, which include, but are not limited to 1) the hybridization between a probe and genomic or cDNA library so as to select a homologous polynucleotide sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain the double-stranded DNA.

Among the above methods, the isolation of genomic DNA is least frequently used. A commonly used method is the direct chemical synthesis of DNA sequence. A more frequently used method is the isolation of cDNA sequence. Standard methods for isolating the cDNA of interest is to isolate mRNA from donor cells that highly express said gene followed by reverse transcription of mRNA to form plasmid or phage cDNA library. There are many established techniques for extracting mRNA and the kits are commercially available (e.g. Qiagene). Conventional method can be used to construct cDNA library (Sambrook, et al., 1989, *Molecular Cloning, A Laboratory Manual, Cold Spring Harbor Laboratory*, New York). The cDNA libraries are also commercially available. For example, Clontech Ltd. has various cDNA libraries. When PCR is further used, even an extremely small amount of expression products can be cloned.

Numerous well-known methods can be used for screening for the polynucleotide of the invention from cDNA library. These methods include, but are not limited to, (1) DNA-DNA or DNA-RNA hybridization; (2) the appearance or loss of the function of the marker-gene; (3) the determination of the level of human polyadenylation binding Protein 20.13 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleotides, preferably at least 30 nucleotides, more preferably at least 50 nucleotides, and most preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. The labels for DNA probe include, e.g., radioactive isotopes, fluoresceins or enzymes such as alkaline phosphatase.

In method (4), the detection of the protein products expressed by human polyadenylation binding Protein 20.13 gene can be carried out by immunology methods, such as Western blotting, radioimmunoassay, and ELISA.

The method of amplification of DNA/RNA by PCR (Saiki, et al. Science 1985; 230:1350–1354) is preferably used to obtain the polynucleotide of the invention. Especially when it is difficult to obtain the full-length cDNA, the method of RACE (RACE-cDNA terminate rapid amplification) is preferably used. The primers used in PCR can be selected according to the polynucleotide sequence information of the invention disclosed herein, and can be synthesized by conventional methods. The amplified DNA/RNA fragments can be isolated and purified by conventional methods such as gel electrophoresis.

Sequencing of polynucleotide sequence of the gene of the invention or its various DNA fragments can be carried out by the conventional dideoxy sequencing method (Sanger et al., 1977, PNAS, 74: 5463–5467). Sequencing of polynucleotide sequence can also be carried out using the commercially available sequencing kits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a genetically engineered host cell transformed with the vector of the invention or directly with the sequence encoding human polyadenylation binding Protein 20.13, and a method for producing the polypeptide of the invention by recombinant techniques.

In the present invention, the polynucleotide sequences encoding human polyadenylation binding Protein 20.13 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., 1987, Gene, 56:125), The pMSXND expression vector for expression in mammalian cells (Lee and Nathans, 1988, J Biol. Chem., 263:3521) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as translation regulatory components.

Methods known in the art can be used to construct an expression vector containing the DNA sequence of human polyadenylation binding Protein 20.13 and appropriate transcription/translation regulatory components. These methods include in vitro recombinant DNA technique, DNA synthesis technique, in vivo recombinant technique and so on (Sambroook, et al., 1989, Molecular Cloning, a Laboratory Manual, cold Spring Harbor Laboratory, New York). The DNA sequence is operatively linked to a proper promoter in an expression vector to direct the synthesis of mRNA. Exemplary promoters are lac or trp promoter of *E.coli*; PL promoter of λ phage; eukaryotic promoters including CMV immediate early promoter, HSV thymidine kinase promoter, early and late SV40 promoter, LTRs of retrovirus, and other known promoters which control gene expression in the prokaryotic cells, eukaryotic cells or viruses. The expression vector may further comprise a ribosome binding site for initiating translation, transcription terminator and the like. Transcription in higher eukaryotes is increased by inserting an enhancer sequence into the vector. Enhancers are cis-acting elements of DNA, usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for *E. coli*.

The skilled in the art know clearly how to select appropriate vectors, transcriptional regulatory elements, e.g., promoters, enhancers, and selective marker genes.

According to the invention, polynucleotide encoding human polyadenylation binding Protein 20.13 or recombinant vector containing said polynucleotide can be transformed or transfected into host cells to construct genetically engineered host cells containing said polynucleotide or said recombinant vector. The term "host cell" means prokaryote, such as bacteria; or primary eukaryote, such as yeast; or higher eukaryotic, such as mammalian cells. Representative examples are bacterial cells, such as *E. coli, Streptomyces, Salmonella typhimurium*; fungal cells, such as yeast; plant cells; insect cells such as *Drosophila* S2 or Sf9; animal cells such as CHO, COS or Bowes melanoma.

Transformation of a host cell with the DNA sequence of invention or a recombinant vector containing said DNA sequence may be carried out by conventional techniques as are well known to those skilled in the art. When the host is prokaryotic, such as *E. coli*, competent cells, which are capable of DNA uptake, can be prepared from cells harvested after exponential growth phase and subsequently treated by the $CaCl_2$ method using procedures well known in the art. Alternatively, $MgCl_2$ can be used. Transformation can also be carried out by electroporation, if desired. When the host is an eukaryote, transfection methods as well as calcium phosphate precipitation may be used. Conventional mechanical procedures such as micro-injection, electroporation, or liposome-mediated transfection may also be used.

The recombinant human polyadenylation binding Protein 20.13 can be expressed or produced by the conventional recombinant DNA technology (Science, 1984; 224:1431), using the polynucleotide sequence of the invention. The steps generally include:

(1) transfecting or transforming the appropriate host cells with the polynucleotide (or variant) encoding human polyadenylation binding Protein 20.13 of the invention or the recombinant expression vector containing said polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatagraphy, and a combination thereof.

The polypeptide of the invention and antagonists, agonists and inhibitors thereof can be directly used for the treatment of diseases, e.g., various malignant tumors or cancers, dermatitis, inflammation, adrenoprival disease and HIV infection and immune system diseases.

Human poly (A)-binding protein (PABP) is an important eukaryotic RNA binding protein, which has an evolutionarily conservative nucleotide binding domain. It regulates translation initiation, mRNA stability and also the length of poly (A) tail in polyadenylation reaction, and must be blocked by messenger ribonucleoprotein (mRNP) in early embryogenesis. PABP plays its role as an important regulator in gene expression by controlling translation initiation.

Grange T. et al. cloned the cDNA of Human poly (A)-binding protein (PABP) in 1999. It is a novel member of terminal oligo pyridine protein family. Members of the family encode complexes involved in translation and especially in translation control of developmental regulation. Development-dependent translation regulation of PABP mRNA is often associated to oligo pyridine in its 5' terminus. Replacement of the cytosine in its capped site by a purine leads to loss of function of its translation regulation. That cytosine and nearly 30 nucleotides around it form a complex which encodes many translation related proteins such as ribosomal proteins, elongation factor 1α and 2 (EF1α and EF2), and is involved in cis-mediated regulation of developmental-dependent translation by translation factors. (Nucl Aci Res, 1987, 15 (12): 4771–4787).

Both polypeptide of this invention and human poly (A) binding protein are human poly (A) binding proteins, having the characteristic sequence of the PABP family as well as similar biological functions. Polypeptide of this invention can regulate the developmental-dependent translation by binding poly (A) tail and regulating the length of poly (A) tail in polyadenylation reaction in vivo. Polypeptide of this invention and nearly 30 nucleotides around can form a complex which encodes many translation related proteins such as ribosomal proteins, elongation factor 1α and 2 (EF1α and EF2). Replacement of the functional site, the cytosine in the capped site by some purine leads to loss or reduction of translation regulation activity of this polypeptide of the invention, and so leads to translation level decrease of ribosomal proteins, elongation factor 1α and 2 (EF1α and EF2)H. As a result, it induces developmental protein translation abnormality and causes related diseases.

As discussed above, abnormal expression of human poly (A) binding protein 20.13 of this invention will cause diseases, especially embryogenesis disorders and growth and developmental disorders. These diseases include but are not limited to:

Embryogenesis disorders: congenital abortion, palatoschisis, absent extemities, limb differentiation disorder, arterial septal defect, arterial septal defect, congenital hydrocephalus, congenital glaucoma or cataract, congenital deafness;

Growth and developmental disorders: mental retardation, brain developmental disorder, skin, fat and muscle dysplasia, bone and knuckle dysplasia, various kinds of metabolic defects, cretinism, dwarfism, Cushing syndrome, sexual hypoevolutism.

Polypeptide of this invention and its antagonists, activators and inhibitors can be directly applied in the treatment of these diseases such as embryogenesis disorders, growth and developmental disorders, some kinds of tumors, inflammations, and immune diseases etc.

The invention also provides methods for screening compounds so as to identify an agent which enhances human polyadenylation binding Protein 20.13 activity (agonists) or decrease human polyadenylation binding Protein 20.13 activity (antagonists). The agonists enhance the biological functions of human polyadenylation binding Protein 20.13 such as inactivation of cell proliferation, while the antagonists prevent and cure the disorders associated with the excess cell proliferation, such as various cancers. For example, in the presence of an agent, the mammal cells or the membrane preparation expressing human polyadenylation binding Protein 20.13 can be incubated with the labeled human polyadenylation binding Protein 20.13 to determine the ability of the agent to enhance or repress the interaction.

Antagonists of human polyadenylation binding Protein 20.13 include antibodies, compounds, receptor deletants and analogues. The antagonists of human polyadenylation binding Protein 20.13 can bind to human polyadenylation binding Protein 20.13 and eliminate or reduce its function, or inhibit the production of human polyadenylation binding Protein 20.13, or bind to the active site of said polypeptide so that the polypeptide can not function biologically.

When screening for compounds as an antagonist, human polyadenylation binding Protein 20.13 may be added into a biological assay. It can be determined whether the compound is an antagonist or not by determining its effect on the interaction between human polyadenylation binding Protein 20.13 and its receptor. Using the same method as that for screening compounds, receptor deletants and analogues acting as antagonists can be selected. Polypeptide molecules capable of binding to human polyadenylation binding Protein 20.13 can be obtained by screening a polypeptide library comprising various combinations of amino acids bound onto a solid matrix. Usually, human polyadenylation binding Protein 20.13 is labeled in the screening.

The invention further provides a method for producing antibodies using the polypeptide, and its fragment, derivative, analogue or cells as an antigen. These antibodies may be polyclonal or monoclonal antibodies. The invention also provides antibodies against epitopes of human polyadenylation binding Protein 20.13. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with human polyadenylation binding Protein 20.13. Various adjuvants, including but are not limited to Freund's adjuvant, can be used to enhance the immunization. The techniques for producing human polyadenylation binding Protein 20.13 monoclonal antibodies include, but are not limited to, the hybridoma technique (Kohler and Milstein. Nature, 1975, 256:495–497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, PNAS, 1985, 81:6851). Furthermore, techniques for producing a single-chain antibody (U.S. Pat. No. 4,946,778) are also useful for preparing single-chain antibodies against human polyadenylation binding Protein 20.13.

The antibody against human polyadenylation binding Protein 20.13 can be used in immunohistochemical method to detect the presence of human polyadenylation binding Protein 20.13 in a biopsy specimen.

The monoclonal antibody specific to human polyadenylation binding Protein 20.13 can be labeled by radioactive isotopes, and injected into human body to trace the location and distribution of human polyadenylation binding Protein 20.13. This radioactively labeled antibody can be used in the non-wounding diagnostic method for the determination of tumor location and metastasis.

Antibodies can also be designed as an immunotoxin targeting a particular site in the body. For example, a monoclonal antibody having high affinity to human polyadenylation binding Protein 20.13 can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill human polyadenylation binding Protein 20.13-positive cells.

The antibody of the invention is useful for the therapy or the prophylaxis of disorders related to the human polyadenylation binding Protein 20.13. The appropriate amount of antibody can be administered to stimulate or block the production or activity of human polyadenylation binding Protein 20.13.

The invention further provides diagnostic assays for quantitative and in situ measurement of human polyadenylation binding Protein 20.13 level. These assays are well known in the art and include FISH assay and radioimmunoassay. The level of human polyadenylation binding Protein 20.13 detected in the assay can be used to illustrate the importance of human polyadenylation binding Protein 20.13 in diseases and to determine the diseases associated with human polyadenylation binding Protein 20.13.

The polypeptide of the invention is useful in the analysis of polypeptide profile. For example, the polypeptide can be specifically digested by physical, chemical, or enzymatic means, and then analyzed by one, two or three dimensional gel electrophoresis, preferably by spectrometry.

New human polyadenylation binding Protein 20.13 polynucleotides also have many therapeutic applications. Gene therapy technology can be used in the therapy of abnormal cell proliferation, development or metabolism, which are caused by the loss of human polyadenylation binding Protein 20.13 expression or the abnormal or non-active expression of human polyadenylation binding Protein 20.13. Recombinant gene therapy vectors, such as virus vectors, can be designed to express mutated human polyadenylation binding Protein 20.13 so as to inhibit the activity of endogenous human polyadenylation binding Protein 20.13. For example, one form of mutated human polyadenylation binding Protein 20.13 is a truncated human polyadenylation binding Protein 20.13 whose signal transduction domain is deleted. Therefore, this mutated human polyadenylation binding Protein 20.13 can bind the downstream substrate without the activity of signal transduction. Thus, the recombinant gene therapy vectors can be used to cure diseases caused by abnormal expression or activity of human polyadenylation binding Protein 20.13. The expression vectors derived from a virus, such as retrovirus, adenovirus, adeno-associated virus, herpes simplex virus, parvovirus, and so on, can be used to introduce the human polyadenylation binding Protein 20.13 gene into the cells. The methods for constructing a recombinant virus vector harboring human polyadenylation binding Protein 20.13 gene are described in the literature (Sambrook, et al. supra). In addition, the recombinant human polyadenylation binding Protein 20.13 gene can be packed into liposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozyme and the oligonucleotides, including antisense RNA and DNA, which inhibit the translation of the human polyadenylation binding Protein 20.13 mRNA. Ribozyme is an enzyme-like RNA molecule capable of specifically cutting certain RNA. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and downstream of the RNA polymerase promoter. In order to increase its stability, a nucleic acid molecule can be modified in many manners, e.g., increasing the length of two the flanking sequences, replacing the phosphodiester bond with the phosphothioester bond in the oligonucleotide.

The polynucleotide encoding human polyadenylation binding Protein 20.13 can be used in the diagnosis of human polyadenylation binding Protein 20.13 related diseases. The polynucleotide encoding human polyadenylation binding Protein 20.13 can be used to detect whether human polyadenylation binding Protein 20.13 is expressed or not, and whether the expression of human polyadenylation binding Protein 20.13 is normal or abnormal in the case of diseases. For example, human polyadenylation binding Protein 20.13 DNA sequences can be used in the hybridization with biopsy samples to determine the expression of human polyadenylation binding Protein 20.13. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for analysis of differential expression of genes in tissues and for the diagnosis of genes. The human polyadenylation binding Protein 20.13 specific primers can be used in RNA-polymerase chain reaction and in vitro amplification to detect transcripts of human polyadenylation binding Protein 20.13.

Further, detection of mutations in human polyadenylation binding Protein 20.13 gene is useful for the diagnosis of human polyadenylation binding Protein 20.13-related diseases. Mutations of human polyadenylation binding Protein 20.13 include site mutation, translocation, deletion, rearrangement and any other mutations compared with the wild-type human polyadenylation binding Protein 20.13 DNA sequence. The conventional methods, such as Southern blotting, DNA sequencing, PCR and in situ blotting, can be used to detect a mutation. Moreover, mutations sometimes affects the expression of protein. Therefore, Northern blotting and Western blotting can be used to indirectly determine whether the gene is mutated or not.

Sequences of the present invention are also valuable for chromosome identification. The sequence is specifically targeted to and can hybridize with a particular location on an individual human chromosome. There is a current need for identifying particular sites of gene on the chromosome. Few chromosome marking reagents based on actual sequence data (repeat polymorphism) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15–35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible from chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effect of the drug. These compositions can be used as drugs in disease treatment.

The invention also provides a pharmaceutical pack or kit comprising one or more containers filled with one or more of the ingredients of the pharmaceutical compositions of the invention. With such container (s) there may be a notice from a governmental agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes. human polyadenylation binding Protein 20.13 is administered in an amount, which is effective for treating and/or prophylaxis of the specific indication. The amount of human polyadenylation binding Protein 20.13 administrated on patient will depend upon various factors, such as delivery methods, the subject health, the judgment of the skilled clinician.

BEST MODE FOR CARRYING OUT THE INVENTION

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Cloning of Human Polyadenylation Binding Protein 20.13 Gene

Total RNA from a human embryonic brain was extracted by the one-step method with guanidinium isocyanate/phenol/chloroform. The poly (A) mRNA was isolated from the total RNA with Quik mRNA Isolation Kit (Qiegene). cDNA was prepared by reverse transcription with 2 μg poly (A) mRNA. The cDNA fragments were inserted into the polyclonal site of pBSK (+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin-Elmer) and ABI 377 Automatic Sequencer (Perkin-Elmer). The sequenced cDNA were compared with the public database of DNA sequences (Genebank) and the DNA sequence of one clone 2347g08 was found to be a novel DNA sequence. The inserted cDNA sequence of clone 2347g08 was dual-directionally sequenced with a serial of synthesized primers. It was indicated that the full length cDNA contained in clone 2347g08 was 1916 bp (SEQ ID NO: 1) with a 552 bp ORF located in positions 23–574 which encoded a novel protein (SEQ ID NO: 2). This clone was named pBS-2347g08 and the encoded protein was named human polyadenylation binding Protein 20.13.

EXAMPLE 2

Homology Search of cDNA Clone

The homology research of the DNA sequence and its protein sequence of human polyadenylation binding Protein 20.13 of the invention were performed by Blast (Basic local Alignment search tool) (Altschul, et al., 1990, J. Mol. Biol.; 215:403–10) in databases such as Genbank, Swissport, etc. The most homologous gene to human polyadenylation binding Protein 20.13 of the invention is known human polyadenylation binding Protein. The Genbank accession number of its encoded protein is X65553. The alignment result of the protein was shown in FIG. 1. Two proteins are highly homologous with an identity of 86% and a similarity of 94%.

EXAMPLE 3

Cloning Human Polyadenylation Binding Protein 20.13 Gene by RT-PCR

The template was total RNA extracted from a human embryonic brain. The reverse transcription was carried out with oligo-dT primer to produce cDNAs. After cDNA purified with Qiagen Kit, PCR was carried out with the following primers:

```
Primer 1:
5'-GAGCCCCGGCCCCCTGCCCACCAT-3'      (SEQ ID NO:3)

Primer 2:
5'-CATAGGCCGAGGCGGCCGACATGT-3'      (SEQ ID NO:4)
```

Primer 1 is the forward sequence started from position 1 of 5' end of SEQ ID NO: 1.

Primer 2 is the reverse sequence of the 3' end of SEQ ID NO: 1.

The amplification condition was a 50 μl reaction system containing 50 mmol/L KCl, 10 mmol/L Tris-Cl (pH8.5), 1.5 mmol/L $MgCl_2$, 200 μmol/L dNTP, 10 pmol of each primer, 1 U Taq DNA polymerase (Clontech). The reaction was performed on a PE 9600 DNA amplifier with the following parameters: 94° C. 30 sec, 55° C. 30 sec, and 72° C. 2 min for 25 cycles. β-actin was used as a positive control, and a blank template, as a negative control in RT-PCR. The amplified products were purified with a QIAGEN kit, and linked with a pCR vector (Invitrogen) using a TA Cloning Kit. DNA sequencing results show that the DNA sequence of PCR products was identical to nucleotides 1–1916 bp of SEQ ID NO: 1.

EXAMPLE 4

Northern Blotting of Expression of Human Polyadenylation Binding Protein 20.13 Gene Total RNA was extracted by one-step method (Anal. Biochem 1987, 162, 156–159) with guanidinium isocyanate-phenol-chloroform. That is, homogenate the organize using 4M guanidinium isocyanate-25 mM sodium citrate, 0.2 sodium acetate (pH 4.0), add 1 volume phenol and ⅕ volume chloroform-isoamyl alcohol (49:1), centrifuge after mixing. Take out the water phase, add 0.8 volume isopropyl alcohol, then centrifuge the mixture. Wash the RNA precipitation using 70% ethanol, then dry, then dissolve it in the water. 20 μg RNA was electrophoresed on the 1.2% agarose gel containing 20 mM 3-(N-morpholino) propane sulfonic acid (pH 7.0)-5 mM sodium acetate-1 mM EDTA-2.2 M formaldehyde. Then transfer it to a nitrocellulose filter. Prepare the $^{32}P$-labelled DNA probe with $\alpha$-$^{32}P$ dATP by random primer method. The used DNA probe is the coding sequence (23 bp–574 bp) of human polyadenylation binding Protein 20.13 amplified by PCR indicated in FIG. 1. The nitrocellulose filter with the transferred RNA was hybridized with the $^{32}P$-labelled DNA probe ($2 \times 10^6$ cpm/ml) overnight in a buffer containing 50% formamide-25 mM $KH_2PO_4$ (pH 7.4)-5× Denhardt's solution and 200 μg/ml salmine. Then wash the filter in the 1×SSC-0.1% SDS, at 55° C., for 30 min. Then analyze and quantitative determinate using Phosphor Imager.

EXAMPLE 5

In vitro Expression, Isolation and Purification of Recombinant Human Polyadenylation Binding Protein 20.13

A pair of primers for specific amplification was designed based on SEQ ID NO: 1 and the encoding region in FIG. 1, the sequences are as follows:

```
                                             (Seq ID NO:5)
Primer 3:   5'-CCCCATATGATGAACGCCAGCGGTTCTGGCTAC-3'

(Seq ID NO:6)
Primer 4:   5'-CCCGAATTCCTATGTGCTGCTGAGGAACATTTG-3'
```

These two primers contain a NdeI and EcoRI cleavage site on the 5' end respectively. Within the sites are the coding sequences of the 5' and 3' end of the desired gene. NdeI and EcoRI cleavage sites were corresponding to the selective cleavage sites on the expression vector pET-28b (+) (Novagen, Cat. No. 69865.3). PCR amplification was performed with the plasmid pBS-2347g08 containing the full-length target gene as a template. The PCR reaction was subject to a 50 μl system containing 10 pg pBS-2347g08 plasmid, 10 pmol of Primer-3 and 10 pmol of Primer4, 1 μl of Advantage polymerase Mix (Clontech). The parameters of PCR were 94° C. 20 sec, 60° C. 30 sec, and 68° C. 2 min for 25 cycles. After digesting the amplification products and the plasmid pET-28 (+) by NdeI and EcoRI, the large fragments were recovered and ligated with T4 ligase. The ligated product was transformed into *E.coli* DH5α cells with the calcium chloride method. After overnight culture on a LB plate containing a final concentration of 30 μg/ml kanamycin, positive clones were selected using colony PCR and then sequenced. The positive clone (pET-2347g08) with the correct sequence was selected and the recombinant plasmid thereof was transformed into BL21 (DE3)plySs (Novagen) using the calcium chloride method. In an LB liquid medium containing a final concentration of 30 μg/ml of kanamycin, the host bacteria BL21 (pET-2347g08) were cultured at 37° C. to the exponential growth phase, then IPTG were added with the final concentration of 1 mmol/L, the cells were cultured for another 5 hours, and then centrifuged to harvest the bacteria. After the bacteria were sonicated, the supernatant was collected by centrifugation. Then the purified desired protein—human polyadenylation binding Protein 20.13 was obtained by a His.Bind Quick Cartridge (Novagen) affinity column with binding 6His-Tag. SDS-PAGE showed a single band at 20.13 kDa (FIG. 2). The band was transferred onto the PVDF membrane and the N terminal amino acid was sequenced by Edams Hydrolysis, which shows that the first 15 amino acids on N-terminus were identical to those in SEQ ID NO: 2.

EXAMPLE 6

Preparation of Antibody Against Human Polyadenylation Binding Protein 20.13

The following specific human polyadenylation binding Protein 20.13 polypeptide was synthesized by a polypeptide synthesizer (PE-ABI): NH2-Met-Asn-Ala-Ser-Gly-Ser-Gly-Tyr-Pro-Leu-Ala-Ser-Leu-Tyr-Val-COOH (SEQ ID NO:7). The polypeptide was conjugated with hemocyanin and bovine serum albumin (BSA) respectively to form two composites (See Avrameas et al., Immunochemistry, 1969, 6:43). 4 mg of hemocyanin-polypeptide composite was used to immunize rabbit together with Freund's complete adjuvant. The rabbit was re-immunized with the hemocyanin-polypeptide composite and Freund's incomplete adjuvent 15 days later. The titer of antibody in the rabbit sera was determined with a titration plate coated with 15 µg/ml BSA-polypeptide composite by ELISA. The total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinity chromatography. The immunoprecipitation approved that the purified antibodies could specifically bind to human polyadenylation binding Protein 20.13.

EXAMPLE 7

Application of the Polynucleotide Fragments of said Invention as Hybrid Probes

Selection of suitable oligonucleotides from the polynucleotide of said invention as hybrid probes can be versatilly applied. The said probe could be used to determine the existence of polynucleotide of said invention or its homologous polynucleotide sequences by hybridization with genome, or cDNA library of normal or clinical tissues from varied sources. The said probes could be further used to determine whether polynucleotide of said invention or its homologous polynucleotide sequences are abnormally expressed in cells from normal or clinical tissues.

The objectives of the following example are to select suitable oligonucletide fragments from the said invented polynuleotide SEQ ID NO:1 as hybird probes to apply in membrane hybridization to determine whether there are polynucleotide of said invention or its homologous polynucleotide sequences in examined tissues. membrane hybridization methods include dot hybridization, Southern blot, Northern blot, and replica hybridization. All these methods follow nearly the same steps after the polynucleotide samples are immobilized on membranes. These same steps are: membranes with samples immobilized on are prehybridized in hybrid buffer not containing probes to block nonspecific binding sites of the samples on membranes. Then prehybrid buffer is replaced by hybrid buffer containing labeled probes and continue incubation at the appropriate temperature so probes hybridize with the target nucleotides. Free probes are washed off by a series of washing steps after the hybrid step. A high-stringency washing condition (relatively low salt concentration and high temperature) is applied in the said example to reduce the hybridization background and remain highly specific signal. Two types of probes are selected for the said example: the first type probes are oligonucleotides identical or annealed to the said invented polynucleotide SEQ ID NO:1; the second type probes are oligonucleotides partially identical or partially annealed to the said invented polynucleotide SEQ ID NO:1. Dot blot method is applied in the said example for immobilization of the samples on membrane. The strongest specific signal produced by hybridization between first type probes and samples is remained after relatively strict membrane washing steps.

Selection of Probes

The principles below should be followed and some things should be taken into consideration for selection of oligonucleotide fragments from the said invented polynucleotide SEQ ID NO:1 as hybrid probes:

1. the optimal length of probes should be between eighteen and fifty nucleotides.
2. GC amount should be between 30% and 70%, since nonspecific hybridization increases when GC amount is more than 70%.
3. there should be no complementary regions within the probes themselves.
4. probes meeting to the requirements above could be initially selected for further computer-aided sequence analysis, which includes homology comparison between said initial selected probes and its sourced sequence region (SEQ ID NO: 1), other known genomic sequences and their complements. Generally, said initial selected probes should not be used when they share fifteen identical continuous base pairs, or 85% homology with non-target region.
5. whether said initial selected probes should be chose for final application relies on further experimental confirmation.

The following two probes could be selected and synthesized after the analysis above:

Probe one belongs to the first type probes, which is completely identical or annealed to the gene fragments of SEQ ID NO: 1 (41 Nt);

(SEQ ID NO:8)
5'-TGAACGCCAGCGGTTCTGGCTACCCGCTTGCCTCGCTTTAC-3'

Probe two belongs to the second type probes which is a replaced or mutant sequence of the gene fragments of SEQ ID NO: 1, or of its complementary fragments (41 Nt):

(SEQ ID NO:9)
5'-TGAACGCCAGCGGTTCTGGCCACCCGCTTGCCTCGCTTTAC-3'

Any other frequently used reagents unlisted but involved in the following concrete experimental steps and their preparation methods can be found in the reference: DNA PROBES G. H. Keller; M. M. Manak; Stockton Press, 1989 (USA) or a more commonly used molecular cloning experimental handbook (molecular cloning) (Sambrook, et al., 1998, Academic press, $2^{nd}$ edition).

Sample Preparation

1) Extract DNA From Fresh or Frozen Tissues

Steps: 1) move the fresh or newly thawy tissue (source tissue of said invented polyucleotide) onto a ice-incubated dish containing phosphate-buffered saline (PBS). Cut the tissue into small pieces with scissors or an operating knife. Tissue should be remained damp through the operation. 2) mince the tissue by centrifugation at 2,000 g for 10 minutes.

3) re-suspend the pellet (about 10 ml/g) with cold homogenating buffer (0.25 mol/l saccharose; 25 mmol/l Tris-HCl, pH7.5; 25 m mol/LnaCl; 25 mmol/L $MgCl_2$. 4) at 4° C., and homogenate tissue suspension at full speed with an electronic homogenizer until it's completely smashed. 5) centrifuge at 1,000 g for 10 minutes. 6) re-suspend the cell pellet (1–5 ml per 0.1 g initial tissue sample), and centrifuge at 1,000 g for 10 minutes. 7) re-suspend the pellet with lysis buffer (1–5 ml per 0.1 g initial tissue sample), and continue to use the phenol extraction method.

2) Phenol Extraction of DNA

Steps: 1) wash cells with 1–10 ml cold PBS buffer and centrifuge at 1000 g for 10 minutes. 2) re-suspend the precipitated cells with at least 100 ul cold cell lysis buffer ($1 \times 10^8$ cells/ml). 3) add SDS to a final concentration of 1%. Addition of SDS into the cell precipitation before cell re-suspension will cause the formation of large balls by cells which is difficult to be smashed and total production will be reduced. This phenomenon is especially severe when extracting more than $10^7$ cells. 4) add protease K to the final concentration of 200 ug/ml. 5) incubate at 50° C. for an hour or shake gently overnight at 37° C. 6) add an equal volume of phenol:chloroform:isoamyl alcohol (25:24:1) to the DNA solution to be purified in a microcentrifuge tube, and centrifuge for 10 minutes. If the two phases are not clearly separated, the solution should be recentrifuged. 7) remove the water phase to a new tube. 8) add an equal volume of chloroform:isoamyl alcohol (24:1) and centrifuge for 10 minutes. 9) remove the water phase containing DNA to a new tube and then purify DNA by ethanol precipitation.

3) DNA Purification by Ethanol Precipitation

Steps: 1) add 1/10 vol of 2 mol/L sodium acetate and 2 vol of cold 100% ethanol into the DNA solution, mix and place at −20° C. for an hour or overnight. 2) centrifuge for 10 minutes. 3) carefully spill the ethanol. 4) add 500 ul of cold 70% ethanol to wash the pellet and centrifuge for 5 minutes. 5)carefully spill the ethanol, add 500 ul cool ethanol to wash the pellets and centrifuge for 5 minutes. 6) carefully spill the ethanol and invert the tube on bibulous paper to remove remnant ethanol. Air dry for 10–15 minutes to evaporate ethanol on pellet surface. But notice not to dry the pellet completely since completely dry pellet is difficult to be dissolved again. 7) re-suspend the DNA pellet with a small volume of TE or water. Spin at low speed or blow with a drip tube, and add TE gradually and mix until DNA is completely dissolved. Nearly add 1 μl TE every $1–5 \times 10^6$ cells.

The following 8–13 steps are applied only when contamination must be removed, otherwise go to step 14 directly. 8) add Rnase A into DNA solution to a final concentration of 100 ug/ml and incubate at 37° C. for 30 minutes. 9) add SDS and protease K to the final concentration of 0.5% and 100 ug/ml individually, and incubate at 37° C. for 30 minutes. 10) add an equal volume of phenol:chloroform:isoamyl alcohol (25:24:1), and centrifuge for 10 minutes. 11) carefully remove out the water phase and extract it with an equal volume of chloroform:isoamyl alcohol (24:1) and centrifuge for 10 minutes. 12) carefully remove out the water phase, and add 1/10 vol of 2 mol/L sodium acetate and 2.5 vol of cold 100% ethanol, then mix and place at −20° C. for an hour. 13) wash the pellet with 70% ethanol and 100% ethanol, air dry and re-suspend DNA as same as the steps 3–6. 14) determine the purity and production of DNA by $A_{260}$ and $A_{280}$ assay. 15) separate DNA sample into several portions and store at −20° C.

Preparation of Sample Membrane

1) Take 4×2 pieces of nitrocellulose membrane (NC membrane) of desired size, and lightly mark out the sample dot sites and sample number with a pencil. Every probe needs two pieces of NC membrane, so then membranes could be washed under high stringency condition and stringency condition individually in the following experimental steps.

2) Suck 15 μl of samples and control individually, dot them on the membrane, and dry at room temperature.

3) Place the membranes on filter paper soaked in 0.1 mol/LNaOH, 1.5 mol/L NaCl, leave for 5 minutes (twice), and allow to dry. Transfer the membranes on filter paper soaked in 0.5 mol/L Tris-HCl (pH7.0), 3 mol/L NaCl, leave for 5 minutes (twice), and allow to dry.

4) Place the membranes between clean filter paper, packet with aluminum foil, and vacuum dry at 60–80° C. for 2 hours.

Labeling of Probes

1) Add 3 ul probe (0.1 OD/10 μl), 2 μl kinase buffer, 8–10 μCi γ-$^{32}$P-dATP+2 U Kinase, and add water to the final volume of 20 μl.

2) Incubate at 37° C. for 2 hours.

3) Add 1/5 vol bromophenol blue indicator (BPB).

4) Load that sample on Sephadex G-50 column.

5) Collect the first peak before the elution of $^{32}$P-Probe (monitor the eluting process by Monitor).

6) Five drops each tube and collect for 10–15 tubes.

7) Measure the isotope amount with liquid scintillator

8) Merged collection of the first peak is the prepared $^{32}$P-Probe (the second peak is free γ-$^{32}$P-dATP)

Prehybridization

Place the sample membranes in a plastic bag, add 3–10 mg prehybrid buffer (10× Denhardts; 6×SSC, 0.1 mg/ml CT DNA (calf thymus gland DNA)), seal the bag, and shake on a 68° C. water bath for two hours.

Hybridization

Cut off a corner of the plastic bag, add in prepared probes, seal the bag, and shake on a 42° C. water bath overnight.

Membrane Washing

Membrane washing applying a high-stringency condition:

1) Take out the hybridized sample membranes

2) Wash the membranes with 2×SSC, 0.1% SDS at 40° C. for 15 minutes (twice).

3) Wash the membranes with 0.1×SSC, 0.1% SDS at 40° C. for 15 minutes (twice).

4) Wash the membranes with 0.1×SSC, 0.1% SDS at 55° C. for 30 minutes (twice), and dry at room temperature.

Membrane Washing Applying a Low-Stringency Condition

1) Take out the hybridized sample membranes.

2) Wash the membranes with 2×SSC, 0.1% SDS at 37° C. for 15 minutes (twice).

3) Wash the membranes with 0.1×SSC, 0.1% SDS at 37° C. for 15 minutes (twice).

4) Wash the membranes with 0.1×SSC, 0.1% SDS at 40° C. for 15 minutes (twice), and dry at room temperature.

X Ray Autoradiography

X ray autoradiograph at −70° C. (autoradiograph time varies according to radioactivity of the hybrid spots)

Experimental Results

In hybridization experiments carried out under low-stringency membrane washing condition, the radioactivity of all the above two probes hybrid spots shows no obvious difference; while in hybridization experiments carried out under high-stringency membrane washing condition, radioactivity of the hybrid spot by probe one is obviously stronger than the other three's. So probe one could be applied in qualitative and quantitative analysis of the existence and differential expression of said invented polynucleotide in different tissues.

---

We claim:

1. An isolated human polyadenylation binding protein 20.13 comprising an amino acid sequence that is at least 95% identical to the amino acid sequence of SEQ ID NO: 2.

2. The protein of claim 1, wherein said protein comprises the amino acid sequence of SEQ ID NO: 2.

* * * * *